United States Patent [19]

Breitner et al.

[11] Patent Number: 5,643,960
[45] Date of Patent: Jul. 1, 1997

[54] METHOD OF DELAYING ONSET OF ALZHEIMER'S DISEASE SYMPTOMS

[75] Inventors: John C. S. Breitner, Chapel Hill; Kathleen A. Welsh, Durham, both of N.C.

[73] Assignee: Duke University, Durham, N.C.

[21] Appl. No.: 228,019

[22] Filed: Apr. 15, 1994

[51] Int. Cl.$^6$ .................... A61K 31/60; A61K 31/615; A61K 31/54; A61K 31/44; A61K 31/425; A61K 31/42; A61K 31/415; A61K 31/40; A61K 31/38; A61K 31/34; A61K 31/195; A61K 31/19

[52] U.S. Cl. .................. 514/570; 514/159; 514/162; 514/165; 514/226.5; 514/356; 514/357; 514/365; 514/370; 514/375; 514/400; 514/404; 514/419; 514/420; 514/423; 514/428; 514/429; 514/448; 514/567; 514/569; 514/471

[58] Field of Search ..................... 514/159, 162, 514/165, 226.5, 356, 357, 365, 370, 375, 400, 404, 419, 420, 423, 428, 429, 448, 567, 569, 471, 570

[56] References Cited

U.S. PATENT DOCUMENTS

| | | | |
|---|---|---|---|
| 5,190,960 | 3/1993 | Guillaumet et al. | 514/318 |
| 5,192,753 | 3/1993 | McGeer et al. | 514/159 |
| 5,225,571 | 7/1993 | Lee | 549/222 |
| 5,229,401 | 7/1993 | Effland et al. | 514/337 |
| 5,258,400 | 11/1993 | Garst et al. | 514/443 |
| 5,258,513 | 11/1993 | Van Keulen et al. | 544/58.2 |
| 5,352,688 | 10/1994 | Kaminski | 514/357 |

OTHER PUBLICATIONS

McGeer et al, "Anti-inflammatory drugs and Alzheimer disease", The Lancet 335:1037 (1990).
Schnabel, J., "New Alzheimer's Therapy Suggested", Science 260:1719 (1993).
Gordon, M.N., "Microglia and Immune Activation in Alzheimer's Disease" J. Florida M.A. 80(4):267 (1993).
Vane, "Towards a better aspirin", Nature 367:215 (1994).
CA 113: 17731, Yanagawa et al, 1990.

Primary Examiner—Kimberly Jordan
Attorney, Agent, or Firm—Nixon & Vanderhye P.C

[57] ABSTRACT

The present invention relates, in general, to a method of preventing or delaying the onset of Alzheimer's disease and related neurodegenerative disorders. The method involves the administration to individuals at risk of developing the disease (or disorder) a non-steroidal anti-inflammatory agent and/or a histamine H2 receptor blocking agent. The invention also relates to a method of treating Alzheimer's disease and related neurodegenerative disorders that involves the use of such agents.

17 Claims, 3 Drawing Sheets

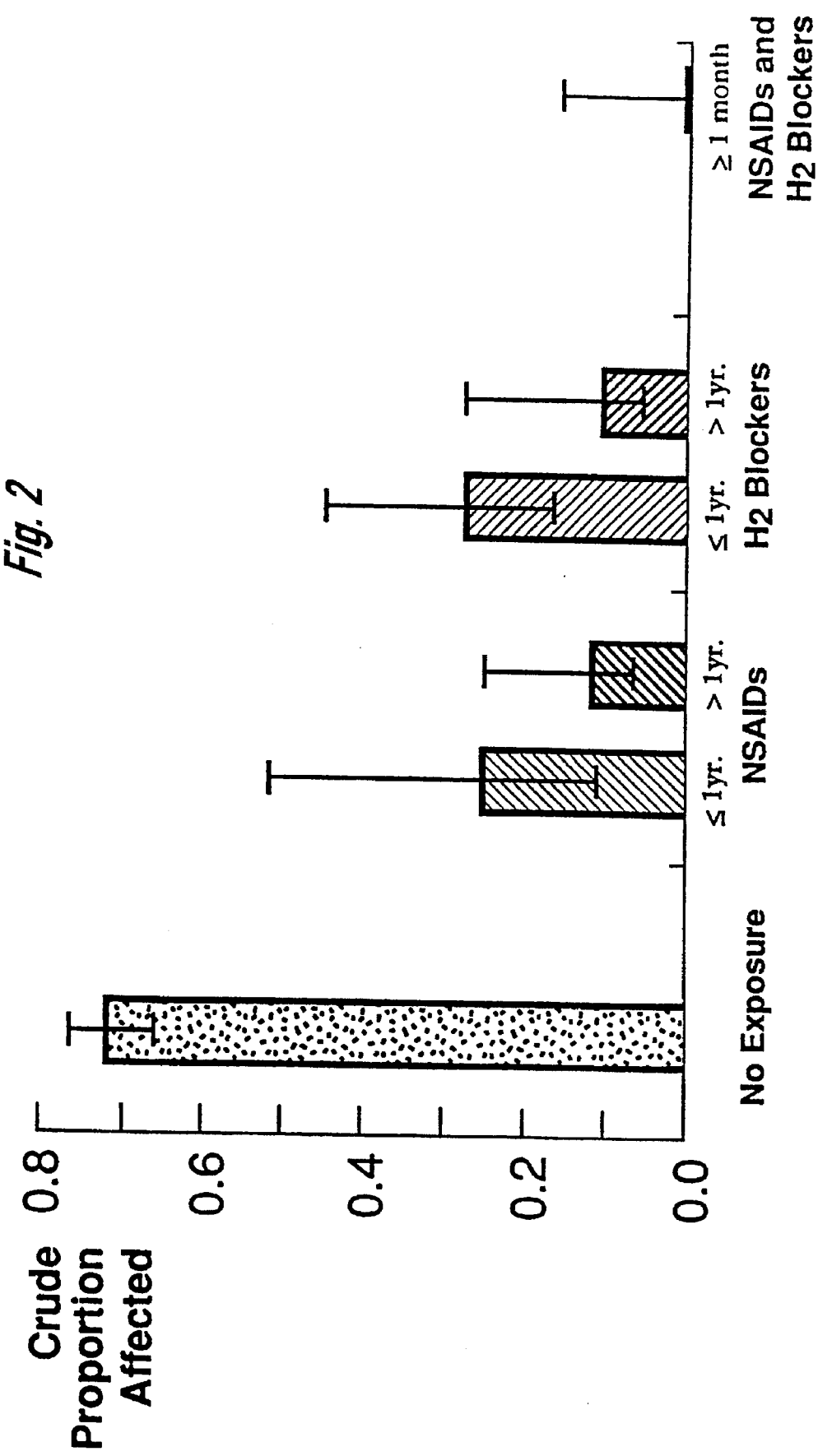

METHOD OF DELAYING ONSET OF ALZHEIMER'S DISEASE SYMPTOMS

This invention was made with Government support under Grant Nos. RO1 AG08549-05 and 5R35AG07822 awarded by the National Institutes of Health. The Government has certain rights in the invention.

FIELD OF THE INVENTION

The present invention relates, in general, to a method of preventing or delaying the onset of Alzheimer's disease and related neurodegenerative disorders. The method involves the administration to individuals at risk of developing the disease a non-steroidal anti-inflammatory agent and/or a histamine H2 receptor blocking agent. The invention also relates to a method of treating Alzheimer's disease that involves the use of such agents.

BACKGROUND

Alzheimer's disease is a progressive neurocognitive disorder which, without preventive intervention, will affect 10% of the developed world's population (Hagnell et al, Neuropsychobiology 7:201 (1981); Katzman et al, Ann. Neurol. 25:317 (1989)). Susceptibility to the disease is strongly influenced by genes. Two forms of this disease have been attributed to mutations on chromosomes 14 and 21 that act as dominant genetic traits (Hardy, Nature Genet. 4:233 (1992), (Schellenberg et al, Science 258:668 (1992), St. George-Hyslop et al, Nature Genet. 2:330 (1992), Van Broeckhoven et al, Nature Genet. 2:335 (1992)). At least two additional forms of Alzheimer's disease are presumed to be caused by dominant mutations located elsewhere in the genome (Pericak-Vance et al, Am. J. Hum. Genet. 48:1034 (1991); Schellenberg et al, Science 241:1507 (1988); Roses et al, Current Neurology 14, C. V. Mosby, Chicago (1994)). In addition, the timing of expression of the disease is strongly influenced by genotype at the polymorphic locus for apolipoprotein E (APOE) on chromosome 19 (Corder et al, Science 261:921 (1993); Corder et al, Nature Genet. (1994)).

The symptoms of Alzheimer's disease appear typically between ages 65 and 90 (Breteler et al, Epidemiol. Rev. 14:59 (1992)) and include deterioration of cognition, memory and language. Since later onset implies briefer and less severe symptoms, if any, before death (Breitner, Ann. Intern. Med. 115:601 (1991)), the identification of factors that delay onset is important. Prior to the present invention, no such factors were securely known, but prior use of glucocorticoids was shown in an exploratory study of twins to be associated with a delay in expression of the disease (Breitner et al, Neurology 44:227 (1994)). A particular method of case-control comparisons in affected twin pairs and other populations at high risk of Alzheimer's disease (Breitner et al, Am. J. Epidemiol. 131:246 (1991)) has resulted in the present invention which provides a novel and highly effective method of preventing Alzheimer's disease or delaying the onset of its symptoms.

BRIEF DESCRIPTION OF THE DRAWINGS

FIG. 2. Alteration in proportion of subjects affected by Alzheimer's disease with exposure to NSAIDS, histamine H2 blockers, or both.

SUMMARY OF THE INVENTION

The present invention relates, in one embodiment, to a method of preventing or delaying the onset of Alzheimer's disease and related neurodegenerative disorders. The method comprises administering to an individual at risk of developing the disease a nonsteroidal anti-inflammatory agent and/or a histamine H2 receptor blocking agent in an amount sufficient to effect the prevention or delay.

The present invention relates, in a further embodiment, to a method of treating the symptoms of Alzheimer's disease, or related neurodegenerative disorder. The method comprises administering to an individual displaying such symptoms an amount of a histamine H2 receptor blocking agent, alone or in combination with a non-steroidal anti-inflammatory agent, sufficient to effect that treatment.

The invention relates, in yet another embodiment, to a composition comprising a histamine H2 receptor blocking agent and a nonsteroidal anti-inflammatory agent.

Advantages of the invention will be clear from the description that follows.

DESCRIPTION OF THE DRAWINGS

Figure 1A:
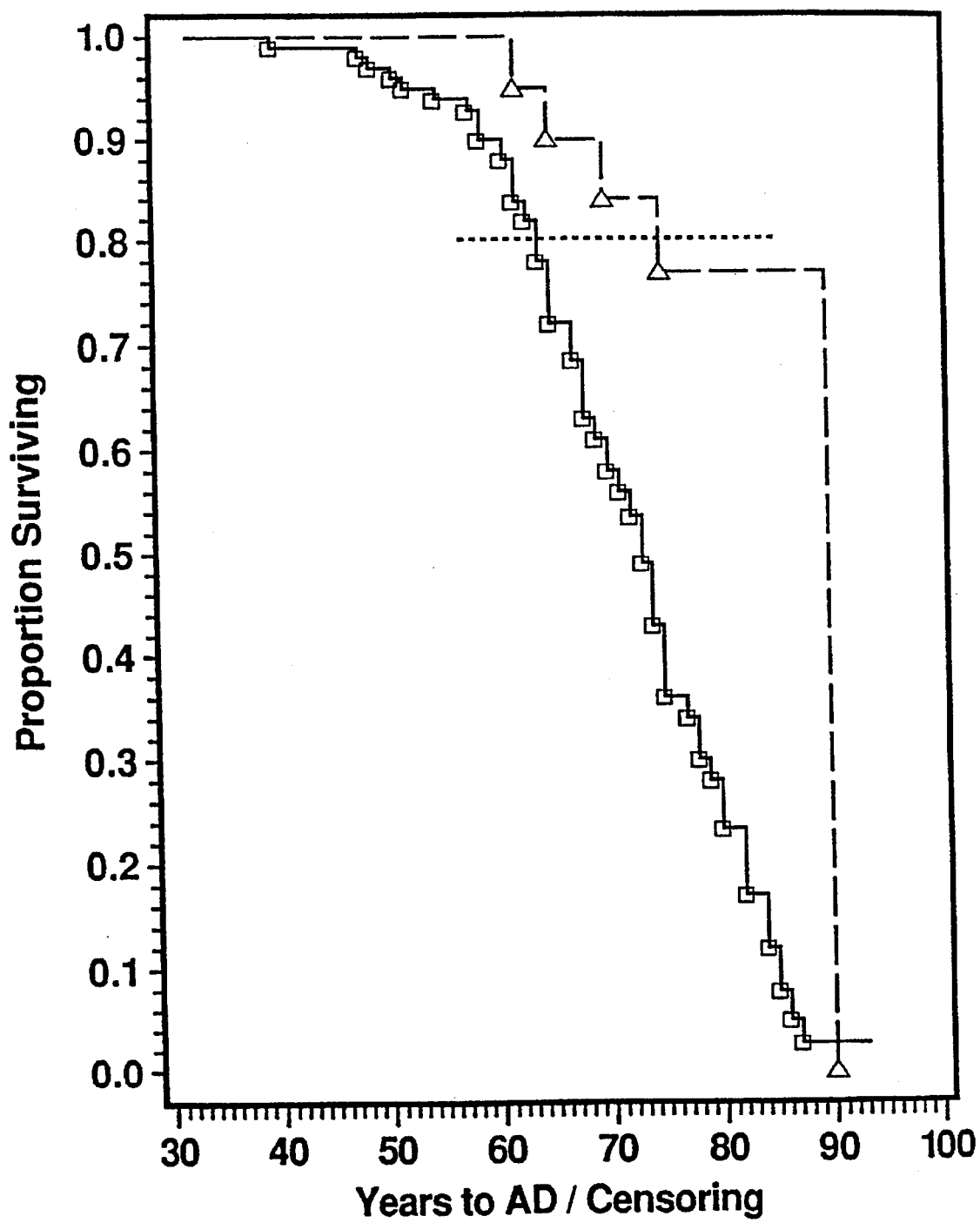
FIG. 1A. Effect of NSAIDS on the probability of disease free survival as a function of age.
Figure 1B:
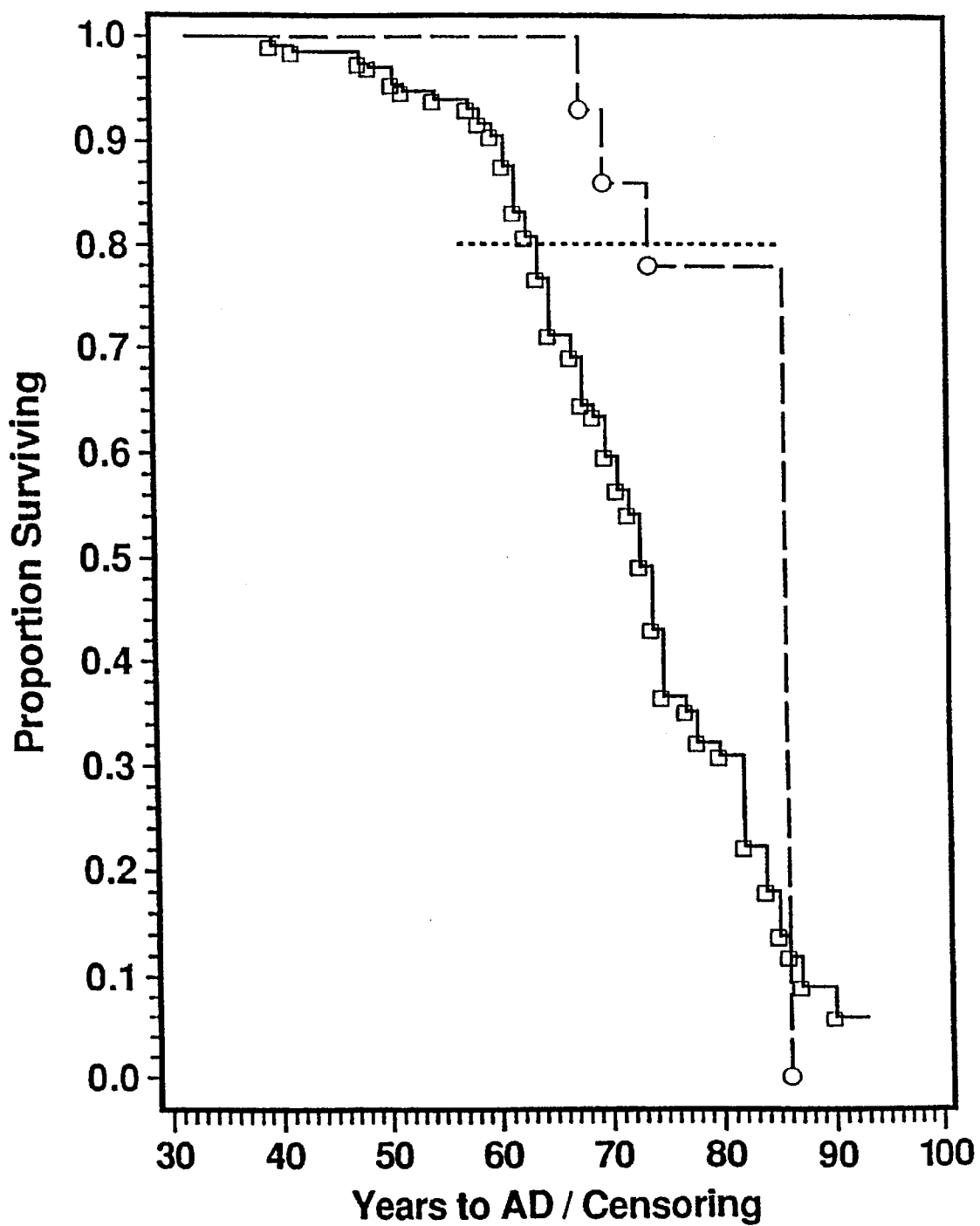
FIG. 1B. Effect of histamine H2 blocking drugs on the probability of disease free survival as a function of age.

FIG. 1. Disease-free survival in subjects categorized by exposure to nonsteroidal anti-inflammatory drugs (NSAIDs) or histamine H2 blocking drugs: FIG. 1A. Effect with NSAIDs. Twenty-one members of sibships with high prevalence of Alzheimer's disease were exposed to NSAIDs for $\geq 1$ month; 110 were not. The survival curves plot the estimated probability of remaining free of disease as a function of age. The squares and triangles at the bottom of each riser in the step-plot indicate the appearance of one or more new cases among the unexposed and exposed groups, respectively. The method intrinsically adjusts for attrition in the sample as older ages are considered. This attrition results from death, prior onset of Alzheimer's disease, or the fact that living subjects have not yet reached the age in question. The cumulative survival estimates are obtained by chain multiplying the individual survival fractions (number surviving free of disease divided by number at risk) at the appearance of each new case through the age in question (Kaplan et al, J. Am. Stat. Assoc. 53:457 (1958)). The cumulative incidence before age 90 in the exposed group is 1 minus the survival fraction of 0.77, or 0.23. The comparable figure for unexposed subjects is 0.98. The difference in lifetime risk in the two groups is highly significant (log rank $\chi^2=14.97$, d.f.=1, p=0.0001). There is a difference of 11 years between the two groups in the age at which a cummulative incidence of 20% is realized. FIG. 1B. Effect with histamine H2 blocking drugs. Twenty-one members of sibships with high prevalence of Alzheimer's disease were exposed to histamine H2 receptor blockers for $\geq 1$ month (circles); 135 were not (squares). The step-plot is generated as in FIG. 1A. There is a 10 year difference between the exposed and unexposed groups' ages at which cumulative incidence of 20% is realized. The difference in the two curves is highly significant (log rank $x^2=9.413$, d.f.=1, p=0.0022).

FIG. 2. Alteration in proportion affected by Alzheimer's disease with exposure to NSAIDs, H2 blockers, or both. Crude proportions of subjects who developed Alzheimer's disease (with standard errors) are shown. Subjects exposed to NSAIDs were evaluated without consideration of exposure to H2 blockers, and vice versa. Reduced proportions of subjects with 1–12 months exposure to NSAIDs or H2 blockers were affected by Alzheimer's disease. With >1 yr. of exposure, the proportions affected were reduced further.

Despite the use of relaxed criteria for exposure (≧1 month duration of treatment), no subject exposed to both types of drugs (not necessarily concurrently) was affected.

DETAILED DESCRIPTION OF THE INVENTION

The present invention relates to a method of preventing or delaying the onset of Alzheimer's disease or related neurodegenerative disorders associated with excitotoxic neuronal cell death (for example, Huntington's disease, amyotrophic lateral sclerosis, epilepsy, Parkinson's disease, and Pick's disease). The method comprises administering to an individual at risk of developing the disease (or disorder) an amount of a nonsteroidal anti-inflammatory agent and/or a histamine H2 receptor blocking agent sufficient to effect the prevention or delay.

The agents used in the present method are sufficiently well tolerated that the method can be used in connection with individuals of low or unknown risk of developing Alzheimer's disease or related disorder. However, the method is preferred for use in connection with individuals at substantial or increased risk, relative to the general population. Individuals at substantial or increased risk include those having a family history of dementia, senility, or Alzheimer's, Parkinson's or Pick's disease. High risk individuals also include those having one or more ϵ4 alleles at the apolipoprotein E (APOE) locus and those lacking an ϵ2 allele at the APOE locus. (See also Hardy, Nature Genet. 4:233 (1992); Schellenberg et al, Science 24:1507 (1988) and Science 258:668 (1992); St. George-Hyslop et al, Nature Genet. 2:330 (1992); Van Broeckhoven et al, Nature Genet. 2:335 (1992); Pericak-Vance et al, Am. J. Hum. Genet. 48:1034 (1991); and Corder et al, Nature Genet. (1994)). The elderly (for example, those over 70 or 75 years old) are also at increased risk.

Nonsteroidal anti-inflammatory agents suitable for use in the present invention include the arylcarboxylic acids (salicylic acid, acetylsalicylic acid, diflunisal, choline magnesium trisalicylate, salicylate, benorylate, flufenamic acid, mefenamic acid, meclofenamic acid and triflumic acid), arylalkanoic acids (diclofenac, fenclofenac, alclofenac, fentiazac, ibuprofen, flurbiprofen, ketoprofen, naproxen, fenoprofen, fenbufen, suprofen, indoprofen, tiaprofenic acid, benoxaprofen, pirprofen, tolmetin, zomepirac, clopinac, indomethacin and sulindac) and enolic acids (phenylbutazone, oxyphenbutazone, azapropazone, feprazone, piroxicam, isoxicam and sudoxicam) described by McGeer (see U.S. Pat. No. 5,192,753); in addition to the arylalkanoic acids McGeer recites, nabumetone, ketorolac and etodolac can also be used. These agents are potent inhibitors of cyclooxygenase (COX). Compounds preferred for use in the present invention include those demonstrating a specificity for inducible cyclooxygenase (COX-2) (Mitchell et al, Proc. Natl. Acad. Sci. USA 90:11693 (1994); Vane, Nature 367:215 (1994); Akarasereenont et al, Br. J. Pharmacol. (1994)), including naproxen and diclofenac (note also BF389 and BW755C), and/or those having a long duration of action, including naproxen, sulindac, nabumetone, phenylbutazone, and piroxicam. Lipid soluble agents are also preferred.

Histamine H2 receptor blocking agents suitable for use in the present invention include cimetidine, ranitidine, famotidine and nizatidine, the more lipid soluble and/or longer acting compounds being preferred.

The amount of nonsteroidal anti-inflammatory agent or histamine H2 receptor blocking agent to be administered and the regimen to be used will vary depending on the agent, or combination of agents, and the individual involved. By way of example, a nonsteroidal anti-inflammatory agent can be administered in a range of 10 mg to 3 g per 100 kg body weight daily or at least 4 times per week. Similarly, and by way of example, a histamine H2 receptor blocking agent can be administered in a range of 5 mg to 2 g per 100 kg body weight daily or at least 4 times per week. These agents are, advantageously, administered virtually continuously starting at an age of about 20 for individuals at high risk (e.g., genetically predisposed individuals) but starting at an age of about 30, 40 or 50, regardless of risk. Although the administration of a nonsteroidal anti-inflammatory agent alone or a histamine H2 receptor blocker alone is effective, it is preferred that both agents be administered, preferably, concurrently.

Histamine H2 receptor blocking agents can be used to treat the symptoms of Alzheimer's disease, and related disorders, as well to delay the onset of the disease (or disorder). When used for treating individuals showing clinical symptoms, the H2 blocking agent is administered, for example, in a dose of 5 mg to 2 g per 100 kg body weight per day. The H2 blocking agents can be used alone or in combination with other agents suitable for use in treating Alzheimer's disease, for example, nonsteroidal anti-inflammatory agents.

Active agents suitable for use in the present method can be formulated as compositions. In addition to the agent, or, as appropriate, pharmaceutically acceptable salt thereof, the composition can comprise a pharmaceutically acceptable carrier. The composition can, depending on the agent, be in a form suitable for, for example, oral, intravenous or intramuscular administration.

While not limiting the invention to any particular mechanism of action, it is noted that both nonsteroidal anti-inflammatory agents and histamine H2 receptor blocking agents may inhibit the pathogenesis of Alzheimer's disease via processes mediated by COX, including excitotory events in the n-methyl-d-aspartate (NMDA) pathway. The principal therapeutic action of nonsteroidal anti-inflammatory agents is suppression of COX (Vane, Nature 367:215 (1994)), and, in particular, the inducible isoform, COX-2, that is responsible for promoting inflammation. COX-dependent events are also part of the calcium-dependent postsynaptic cascade that follows stimulation of glutamate receptors specific for NMDA (Lerea et al, Neuron 10:31 (1993)). Under aberrant conditions (eg, excessive stimulation), the NMDA pathway can induce excitotoxic cell death (Choi, Neuron 1:623 (1988)). Both the oxidation of arachidonic acid to prostaglandins (which requires COX) (Lerea et al, Neuron 10:31 (1993)) and the concomitant generation of superoxide anions appear to be involved in this excitotoxic process (Shearman et al, Proc. Natl. Acad. Sci. USA 11:1470 (1994)). The NMDA response is potentiated by histaminergic activation of H2 receptors (Sunami et al, Methods Find. Exp. Clin. Pharmacol. 13:85 (1991)), and possibly H3 (Bekkers, Science 261:104 (1993)) receptors (the effect of H2 blockers on the latter in the central nervous system being presently unknown). The fact that both nonsteroidal anti-inflammatory agents and H2 blockers prevent or delay the onset of Alzheimer's may result from the involvement of COX and the NMDA pathway in development of the disease. That being the case, inhibition of Alzheimer's disease pathogenesis can be expected to be effected using compounds, other than those described above, that similarly impact on the NMDA pathway and thereby protect against neuronal cell death that may underlie the neurodegeneration of Alzheimer's disease and related disorders.

The non-limiting Examples that follow describe, in some detail, the studies that resulted in the present invention. Briefly, doubly affected sib pairs with Alzheimer's disease onset ages that differed by at least 3 years were studied, as were disease-discordant siblings whose unaffected sib(s) had survived at least 3 years beyond the onset age of the affected sib. Premorbid exposures to steroids, NSAIDs and other treatments were assessed for 186 subjects (91% response rate) by focused retrospective interviews using appropriate blinding and multiple informants when possible. Survival analysis methods were used to compare age-adjusted risk of Alzheimer's disease among sibs who had been exposed or unexposed, before onset, to glucocorticoids, aspirin, non-aspirin NSAIDs, and histamine H2 receptor blockers. The estimated odds ratios (o.r.) with these exposures were 0.54, 0.35 (p=0.04), 0.14 (p=0.01), and 0.15 (p=0.002), respectively, indicating that each type of drug was more commonly used in unaffected or late-affected sibs. The odds ratios for steroids, aspirin and non-aspirin NSAIDs fell within the related confidence interval from the prior twin study (Breitner, Neurology 44:227 (1994)).

In this high risk sample, subjects not exposed to NSAIDs experienced a 98% cumulative incidence of Alzheimer's disease (s.e. 2%) by age 90, compared with 23% (s.e. 11%) for those who had taken NSAIDs (p=0.0001). Unexposed subjects realized a 20% cumulative incidence by age 64, 11 years before exposed individuals. An inverse association between the prior use of histamine H2 blocking drugs and Alzheimer's disease was also found. The age-adjusted lifetime risk of disease among those exposed to histamine H2 blocking drugs was also significantly reduced (p=0.002). The effects with both NSAIDs or aspirin and H2 blockers increased with duration of exposure. The two effects appeared to be additive or complementary, such that no subject who had taken both NSAIDs and H2 blockers developed Alzheimer's disease. The inverse association of Alzheimer's disease with exposure to NSAIDs appeared to be stronger after age 70, and in subjects without an ε4 allele at the polymorphic genetic locus for APOE. The inverse association with H2 blockers showed no strong interaction with age but was stronger in subjects whose genotype included at least one ε4 allele at APOE.

EXAMPLES

The following methodology is relevant to the Examples that follow.

Doubly affected sib pairs with Alzheimer's disease onset ages that differed by at least 3 years were studied, as were disease-discordant siblings whose unaffected sib(s) had survived at least 3 years beyond the onset age of the affected sib. Diagnoses and ages at onset of Alzheimer's disease were established by consideration of all relevant data, including extensive longitudinal observation, laboratory testing, and autopsy confirmation when available. Arthritis, peptic ulcer disease, and other non-neurological conditions were not considered when making these diagnoses. Subjects or their collateral informants received a letter, followed by a structured telephone interview, that investigated several common medical conditions (arthritis, diabetes, peptic ulcer disease) and treatments (glucocorticoids, nonsteroidal anti-inflammatories, including aspirin, acetaminophen, narcotic analgesics, insulin and oral hypoglycemic drugs, and histamine H2 blocking agents). The interview also sought timing and duration of exposure. The interviewers generally knew which subjects had Alzheimer's disease but were blinded to early- or late-affected status. The respondents were not made aware of the hypothesis under investigation. Collateral informants supplied data for the 107 subjects who had developed Alzheimer's disease. Collateral information was also sought for the remaining subjects; however, it is was necessary to rely on autobiographical data from 20 (26%).

EXAMPLE I

Delay or Prevention of Onset of Alzheimer's Disease with Nonsteroidal Anti-inflammatory Agents Like dizygous twins, siblings share 50% of their genetic make-up on average. The relation of Alzheimer's disease onset and prior use of anti-inflammatory drugs was therefore studied in a sample of 186 sibs from 45 pedigrees ascertained for genetic linkage studies of late onset Alzheimer's disease (Pericak-Vance et al, Am. J. Hum. Genet. 48:1034 (1991)). The selected sibs were members of onset-discordant doubly affected pairs or disease-discordant pairs meeting criteria described above. Characteristics of the sample are displayed in Table 1.

TABLE 1

| Characteristics of affected and unaffected sibs | | | |
|---|---|---|---|
| Status | number | no. deceased | censoring age or onset* |
| Affected | 107 | 63 | 69.1 (9.4 yrs.) |
| Unaffected | 79 | 13 | 74.0 (9.5 yrs.) |
| Totals | 186 | 76 | 71.2 (9.8 yrs.) |

*mean (s.d.); Censoring age is age at death, or current age if living.

FIG. 1A. shows Kaplan-Meier survival curves (Kaplan et al, J. Am. Stat. Assoc. 53:457–481 (1958)) for the subjects categorized by prior exposure to NSAIDs. Because of the possibility of disproportionate reporting of exposures in autobiographical information, only the results from the subjects with collateral informants are presented. Similar results were seen when autobiographical data were included. The horizontal line at 20% cumulative incidence of Alzheimer's disease (as a typical example) is intersected 11 years later in exposed subjects. The lifetime age-adjusted risk of Alzheimer's disease in the exposed group is substantially lower (log rank $\chi^2$=14.97, d.f.=1, p=0.0001).

These differences and the association of Alzheimer's disease with the remaining exposures were investigated using a Cox proportional hazards models (Cox, J. Roy. Stat. Soc. (Series B) 34:248–275 (1972)) in which the sample was first stratified by sibship. Table 2 reports odds ratios (o.r), the customary measure of risk associated with an exposure in case-control work. The o.r. is ordinarily calculated as the ratio of proportions exposed versus unexposed in the affected and unaffected groups; for conditions like Alzheimer's disease with age-dependent expression (Breitner et al, Am. J. Epidemiol. 128:536–548 (1988)), the o.r. is preferably calculated using proportional hazards or similar models which consider subjects' current age or age at death (i.e., censoring age), or age at onset of Alzheimer's disease. An o.r. of less than 1 implies reduced risk of disease with exposure. For example, the o.r. of 0.136 with NSAIDs indicates that NSAID users experienced slightly less than 1/7 the age-adjusted risk of non-users. The apparent effect of both aspirin and NSAIDs increased with duration of exposure; the o.r. with use of NSAIDs for >1 yr. (median duration of exposure 5 yrs, mean 9.18, s.d. 8.78 yrs) was 0.075 (p=0.0001), indicating that long term users of these drugs had less than one-tenth the risk of non-users for developing Alzheimer's disease.

TABLE 2

Odds ratios for age-adjusted risk of Alzheimer's disease with exposures to several anti-inflammatory or analgesic drugs

| Exposure | Source of data* | Proportion exposed | Odds ratio (95% c.i.) | p value[+] |
|---|---|---|---|---|
| Glucocorticoids | COL only | 6/130 | 0.542 (0.114–2.570) | 0.4405 |
| Glucocorticoids | COL + AU | 9/151 | 0.569 (0.123–2.633) | 0.4703 |
| NSAIDs | COL only | 21/131 | 0.136 (0.031–0.588) | 0.0076 |
| NSAIDs | COL + AU | 26/151 | 0.116 (0.027–0.495) | 0.0036 |
| NSAIDS (women) | COL + AU | 17/96 | 0.181 (0.056–0.580) | 0.0040 |
| NSAIDs (men) | COL + AU | 9/55 | 0.293 (0.068–1.258) | 0.0987 |
| NSAIDs (exposed 1–12 mo.) | COL + AU | 4/129 | 0.188 (0.024–1.491) | 0.1450 |
| NSAIDS (exposed >1 yr.) | COL + AU | 17/142 | 0.075 (0.022–0.261) | 0.0001 |
| NSAIDs (censoring age $\leq 70$) | COL + AU | 7/56 | 0.583 (0.179–1.899) | 0.3708 |
| NSAIDs (censoring age > 70) | COL + AU | 19/76 | 0.180 (0.043–0.762) | 0.0198 |
| NSAIDs (no APOE $\epsilon 4$ allele) | COL + AU | 15/48 | 0.112 (0.015–0.874) | 0.0366 |
| ($\geq 1$ $\epsilon 4$ allele) | COL + AU | 11/84 | 0.556 (0.200–1.547) | 0.2611 |
| NSAIDs (Alzheimer's disease since 1980 only) | COL + AU | 26/124 | 0.149 (0.034–0.653) | 0.0115 |
| NSAIDs (affected subjects only) | COL only | 5/58 | 0.272 (0.031–2.367) | 0.2381 |
| Aspirin | COL only | 31/136 | 0.349 (0.130–0.938) | 0.0368 |
| Aspirin | COL + AU | 40/157 | 0.343 (0.139–0.844) | 0.0199 |
| Aspirin (exposed 1–12 mo.) | COL + AU | 4/121 | 0.625 (0.086–4.558) | 0.6410 |
| Aspirin (exposed >1 yr.) | COL + AU | 35/152 | 0.369 (0.171–0.796) | 0.0123 |
| Acetaminophen | COL only | 10/131 | 0.157 (0.020–1.222) | 0.0770 |
| Acetaminophen | COL + AU | 17/152 | 0.104 (0.014–0.787) | 0.028 |
| Narcotics | COL only | 1/134 | 0.876 (0.082–9.396) | 0.9129 |
| Narcotics | COL + AU | 1/134 | 0.876 (0.082–9.396) | 0.9129 |

*AU = autobiographical; COL = collateral informant(s); [+]probability of observed data under null hypothesis (o.r. = 1.0: from Cox proportional hazards models.

The criterion for regular exposure to NSAIDs, aspirin, and other oral medications was ingestion on 4 or more days a week for at least one month continuously, at any time up to one year prior to onset of Alzheimer's disease. Exposure to glucocorticoids meant regular use of oral agents for at least a month, or multiple doses of injectable depot agents (e.g., hydrocortisone, betamethasone or triamcinolone acetate suspensions, triamcinolone acetonide suspension). The table reports results with data from collateral informants and also, for comparison, results with addition of autobiographical data from unaffected subjects lacking collaterals. To improve statistical power, the latter method was also used for stratified analyses of main effects or for analyses of interactions. Genotype at APOE was determined using the polymerase chain reaction and restriction fragmentation isotyping, as previously described (Saunders et al, Neurology 43:1467–1472 (1993)). The sample was stratified by sibship, except for male vs. female, young vs. old, and APOE genotype comparisons. Owing to small numbers available, simple odds ratios instead of those derived from proportional hazards models are given for dose-response effects with NSAIDs and aspirin. The variable numbers in the denominators for proportion exposed reflect results of stratification or of variable numbers of subjects with missing data.

EXAMPLE II

Studies of Specificity: Additional Effect with Histamine H2 Blockers

The specificity of the effect with NSAIDs was examined by assessing the interrelation of Alzheimer's disease, NSAIDs and the other medical conditions or treatments ascertained at the same interview (Table 3). Because of the likelihood that subjects using non-aspirin NSAIDs would also have used aspirin, an orthogonal comparison was set up of the effect of aspirin only, as contrasted with effect of NSAIDs but no aspirin, with the use of both, or of neither. Aspirin alone appeared to produce a weak but similar effect to NSAIDs. Acetaminophen (paracetamol) was taken in higher doses than aspirin, which was used mostly in low dose for prevention of heart disease. Acetaminophen alone, which has only a weak anti-inflammatory action (Mitchell et al, Proc. Natl. Acad. Sci. USA 90:11693–11697 (1993)), showed a comparable but statistically inconclusive effect.

TABLE 3

Odds ratios for age-adjusted risk of Alzheimer's disease with NSAIDs with several other variables and effects with Histamine H2 receptor blockers*

| Exposure or condition | Proportion exposed | Odds ratio (95% c.i.) | p value+ |
|---|---|---|---|
| Aspirin, no NSAIDs | 22/123 | 0.508 (0.260–0.990) | 0.0465 |
| NSAIDs, no aspirin | 14/115 | 0.185 (0.058–0.0591) | 0.0044 |
| Aspirin and NSAIDs | 8/109 | 0.143 (0.020–1.030) | 0.0535 |
| Acetaminophen, no NSAIDs | 7/125 | 0.192 (0.027–1.383) | 0.1014 |
| NSAIDs, no acetaminophen | 14/132 | 0.173 (0.054–0.552) | 0.0031 |
| Acetaminophen and NSAIDs | 7/125 | 0.252 (0.035–1.816) | 0.1712 |
| Arthritis (all) | 62/168 | 0.454 (0.242–0.852) | 0.0139 |
| Arthritis, no NSAIDs | 28/123 | 0.758 (0.423–1.358) | 0.3517 |
| NSAIDs, no arthritis | 4/99 | 0 (model indeterminate) | na |
| Arthritis and NSAIDs | 21/116 | 0.252 (0.101–0.629) | 0.0031 |
| Adult onset diabetes (all) | 17/185 | 0.505 (0.203–1.257) | 0.1422 |
| Use of insulin, oral hypoglycemics | 14/185 | 0.526 (0.191–1.447) | 0.2135 |
| Diabetes, no glucocorticoids | | 0.695 (0.334–1.448) | 0.3319 |
| Glucocorticoids, no diabetes | 9/136 | 0.434 (0.106–1.772) | 0.2448 |
| Diabetes and glucocorticoids | 0/127 | 0 (model indeterminate) | na |
| History of peptic ulcer disease (all) | 26/184 | 0.667 (0.296–1.501) | 0.3278 |
| Peptic ulcer disease, no NSAIDs | 16/124 | 0.566 (0.228–1.403) | 0.2190 |
| NSAIDs, no peptic ulcer disease | 22/130 | 0.178 (0.065–0.489) | 0.0008 |
| Peptic ulcer disease and NSAIDs | 4/112 | 0.534 (0.074–3.858) | 0.5344 |
| Histamine H2 blockers (all) | 29/180 | 0.149 (0.044–0.501) | 0.0021 |
| Peptic ulcer disease, no H2 blockers | 9/149 | 1.656 (0.542–5.063) | 0.3760 |
| H2 blockers, no peptic ulcer disease | 15/155 | 0.224 (0.052–0.974) | 0.0460 |
| H2 blockers and peptic ulcer disease | 14/154 | 0.090 (0.011–0.703) | 0.0217 |
| Histamine H2 blockers, no NSAIDs | 18/124 | 0.242 (0.076–0.768) | 0.0161 |
| NSAIDs, no histamine H2 blockers | 19/125 | 0.261 (0.105–0.648) | 0.0038 |
| Histamine H2 blockers and NSAIDs | 7/113 | 0 (model indeterminate) | na |
| Histamine H2 blockers (women) | 16/114 | 0.168 (0.041–0.685) | 0.0129 |
| Histamine H2 blockers (men) | 13/66 | 0.255 (0.061–1.071) | 0.0620 |
| Histamine H2 blockers (exposed 1–12 mo.) | 11/162 | 0.203 (0.057–0.716) | 0.0209 |
| Histamine H2 blockers (exposed >1 yr.) | 10/161 | 0.060 (0.012–0.298) | 0.0009 |
| Histamine H2 blockers (censoring age >70) | 11/64 | 0.180 (0.043–0.743) | 0.0177 |
| Histamine H2 blockers (censoring age ≦70) | 18/93 | 0.254 (0.061–1.062) | 0.0604 |
| Histamine H2 blockers (no APOE ε4 allele) | 14/61 | 0.411 (0.094–1.788) | 0.2360 |
| Histamine H2 blockers (≧1 ε4 allele) | 15/96 | 0.195 (0.048–0.799) | 0.0231 |
| Histamine H2 blockers (Alzheimer's disease since 1980 only) | 29/150 | 0.294 (0.080–1.075) | 0.0643 |
| Histamine H2 blockers (affected subjects only) | 4/72 | 0.758 (0.125–4.606) | 0.7637 |

*collateral data where available, otherwise autobiographical data
,+as in table 2, except orthogonal comparisons not stratified by sibship.
Dose-response effect for H2 blockers was examined by calculation of simple odds ratios, owing to insufficient data for meaningful modeling.

Likewise, the question of whether the effects with NSAIDs reflected their association with underlying medical conditions, rather than the drugs themselves, was addressed. Among the three common ailments, only a past history of arthritis was significantly associated with reduced risk of Alzheimer's disease. The latter association was vitiated, however, in orthogonal analyses of arthritis without use of NSAIDs. There was no significant association of Alzheimer's disease risk with diabetes or its treatments, despite the availability of adequate power to detect such associations (proportion treated 15/164).

Similarly, there was no significant association of Alzheimer's disease and peptic ulcer disease, but an unexpected finding was strong reduction in risk among those with prior use of histamine H2 receptor blocking drugs commonly prescribed for this condition (proportion exposed 29/180, see FIG. 1B.). As with aspirin and NSAIDs, the effect with H2 blockers showed an increase in strength with duration of treatment (median in those with >1 yr. of exposure 5 yrs., mean 7.60, s.d. 7.21 yrs.). Because H2 blockers are sometimes used to reduce gastric irritation from NSAIDs, an orthogonal analysis of H2 blockers and NSAIDs was conducted. The effect with H2 blockers was not explained by use of NSAIDs, and the effects on Alzheimer's disease risk with the two treatments supplemented each other.

FIG. 2 demonstrates a progressive reduction in proportion affected by Alzheimer's disease as subjects reported increasing exposure to both NSAIDs and H2 blockers. The corresponding odds ratios are given in Tables 2 and 3 above. No cases of Alzheimer's disease occurred among the seven individuals who had taken both types of drug for a month or more (compared with disease occurrence in unexposed subjects, Fisher's exact p=0.0003).

EXAMPLE III

Further Analyses: Stratification by Age, Sex, and Genotype at APOE

The question was addressed as to whether individuals with Alzheimer's disease onset before 1980, unlike their later-affected or unaffected sibs, might necessarily have had little exposure to NSAIDs or H2 blockers, since these drugs have been widely prescribed only for the past 15–20 years. One analysis therefore disregarded Alzheimer's disease with onset prior to 1980, but found similar results (see Tables 2 and 3 above).

Analyses of affected individuals only, which avoids the possibility that unaffected comparands bore no predisposition to disease, yielded o.r.'s congruent with the notion that NSAIDs or H2 blockers delay onset of Alzheimer's disease in those predisposed to disease (Tables 2 and 3 above). The displacement of these o.r.'s toward the null value of 1.0 probably reflects truncation in selection of the subjects (ignoring those with greatest delay of onset resulting in death before disease expression). These analyses, as well as that of Alzheimer's disease with glucocorticoids, were statistically inconclusive, presumably because of limited numbers of subjects exposed (e.g., only 3 members of doubly affected pairs had been exposed to NSAIDs).

Trends were observed suggesting that the effect with NSAIDs is stronger in subjects with onset or censoring after age 70 (interaction p=0.22), and in those who lack an ε4 allele at APOE (interaction p=0.13). The modest difference between male and female subjects likely reflects the greater proportion of females at later ages (thus clarifying the confounded effects of age and sex in the previous twin sample, which included mostly older females and younger males). No differences were apparent in the effect with H2 blockers among contrasting strata of age or sex, but there was a moderate trend toward increasing effect among those with at least one ε4 allele. Larger numbers of subjects are required to test further the phenomenon of opposite directionality of drug—APOE interaction with H2 blockers and NSAIDs.

All documents cited above are hereby incorporated in their entirety by reference.

One skilled in the art will appreciate from a reading of this disclosure that various changes in form and detail can be made without departing from the true scope of the invention.

What is claimed is:

1. A method of delaying the onset of Alzheimer's disease symptoms comprising:
    i) identifying an individual at risk of developing said disease;
    ii) administering to said individual an amount of a non-steroidal anti-inflammatory agent sufficient to effect said delay; and
    iii) monitoring said individual for the development of clinical symptoms of said disease.

2. The method according to claim 1 wherein said individual is genetically predisposed to said disease.

3. The method according to claim 1 wherein said individual has a family history of Alzheimer's disease.

4. The method according to claim 1 wherein said individual has at least one ε4 allele at the genetic locus for apolipoprotein E or lacks an ε2 allele at the genetic locus for apolipoprotein E.

5. The method according to claim 1 wherein said individual is over about 60 years old and free of clinical symptoms of Alzheimer's disease.

6. The method according to claim 1 wherein said anti-inflammatory agent is administered to said individual from an age of 20 or older and prior to onset of clinical symptoms of said disease.

7. The method according to claim 6 wherein said anti-inflammatory agent is administered to said individual from an age of 40 or older and prior to onset of clinical symptoms of said disease.

8. A method of delaying the onset of Alzheimer's disease symptoms comprising:
    i) identifying an individual at risk of developing said disease;
    ii) administering to said individual an amount of a histamine H2 receptor blocking agent sufficient to effect said delay; and
    iii) monitoring said individual for the development of clinical symptoms of said disease.

9. The method according to claim 8 wherein said individual is genetically predisposed to said disease.

10. The method according to claim 8 wherein said individual has a family history of Alzheimer's disease.

11. The method according to claim 8 wherein said individual has at least one ε4 allele at the genetic locus for apolipoprotein E or lacks an ε2 allele at the genetic locus for apolipoprotein E.

12. The method according to claim 8 wherein said individual is about 60 years old or older and free of clinical symptoms of Alzheimer's disease.

13. The method according to claim 8 wherein said H2 blocking agent is administered to said individual from an age of 20 or older and prior to onset of clinical symptoms of said disease.

14. The method according to claim 13 wherein said H2 blocking agent is administered to said individual from an age of 40 or older and prior to onset of clinical symptoms of said disease.

15. A method delaying the onset of Alzheimer's disease symptoms comprising:
    i) identifying an individual at risk of developing said disease;
    ii) administering to said individual an amount of a non-steriodal anti-inflammatory agent and a histamine H2 receptor blocking agent sufficient to effect said delay; and
    iii) monitoring said individual for the development of clinical symptoms of said disease.

16. The method according to claim 15 wherein said anti-inflammatory agent and said H2 blocking agent are administered concurrently.

17. The method according to claim 15 wherein said anti-inflammatory agent is naproxen.

* * * * *